(12) United States Patent
Van Haeren et al.

(10) Patent No.: US 10,836,709 B2
(45) Date of Patent: Nov. 17, 2020

(54) PROCESS TO PREPARE A SOLID COMPOSITION OF AN AMINO ACID DIACETIC ACID

(71) Applicant: NOURYON CHEMICALS INTERNATIONAL B.V., Arnhem (NL)

(72) Inventors: Paulus Johannes Cornelis Van Haeren, Doetinchem (NL); Roy Doppen, Deventer (NL); Elwin Schomaker, Arnhem (NL); Raymond Jean Cécile Vaessen, Herkenbosch (NL); Marco Ypma, Duiven (NL); Stijn Oudenhoven, Deventer (NL); Martin Heus, Arnhem (NL)

(73) Assignee: NOURYON CHEMICALS INTERNATIONAL B.V., Arnhem (NL)

( * ) Notice: Subject to any disclaimer, the term of this patent is extended or adjusted under 35 U.S.C. 154(b) by 0 days.

(21) Appl. No.: 16/629,259

(22) PCT Filed: Jul. 3, 2018

(86) PCT No.: PCT/EP2018/067919
§ 371 (c)(1),
(2) Date: Jan. 7, 2020

(87) PCT Pub. No.: WO2019/007943
PCT Pub. Date: Jan. 10, 2019

(65) Prior Publication Data
US 2020/0131115 A1 Apr. 30, 2020

(30) Foreign Application Priority Data
Jul. 7, 2017 (EP) ..................... 17180157

(51) Int. Cl.
C07C 227/42 (2006.01)
C07C 229/24 (2006.01)

(52) U.S. Cl.
CPC ........ C07C 227/42 (2013.01); C07B 2200/13 (2013.01); C07C 229/24 (2013.01)

(58) Field of Classification Search
CPC ... C07C 227/42; C07C 229/24; C07C 229/16; C07C 227/00; C07C 229/04; C07B 2200/13
See application file for complete search history.

(56) References Cited

U.S. PATENT DOCUMENTS 8,748,366 B2 6/2014 Mrzena et al.
9,012,684 B2 4/2015 Moore, Jr. et al.
2011/0288332 A1 11/2011 Moore, Jr. et al.
2012/0046491 A1 2/2012 Mrzena et al.
2012/0071381 A1 3/2012 Mrzena et al.
2012/0149936 A1 6/2012 Baranyai
2013/0053296 A1 2/2013 Baranyai
2014/0155646 A1* 6/2014 Mrzena ................ C07C 227/42
560/171

FOREIGN PATENT DOCUMENTS

| CN | 101578258 A | 11/2009 |
|---|---|---|
| CN | 102458635 A | 5/2012 |
| CN | 102906062 A | 1/2013 |
| WO | 2009103822 A1 | 8/2009 |
| WO | 2010133617 A1 | 11/2010 |
| WO | 2010133618 A1 | 11/2010 |
| WO | WO2010133618 * | 11/2010 |
| WO | 2011023382 A1 | 3/2011 |
| WO | 2011079940 A1 | 7/2011 |
| WO | 2012000915 A1 | 1/2012 |
| WO | 2012150155 A1 | 11/2012 |
| WO | 2012168739 A1 | 12/2012 |
| WO | 2014086662 A1 | 6/2014 |
| WO | 2014090942 A1 | 6/2014 |
| WO | 2014090943 A1 | 6/2014 |
| WO | 2015036324 A1 | 3/2015 |
| WO | 2015121170 A1 | 8/2015 |
| WO | 2015173157 A1 | 11/2015 |

OTHER PUBLICATIONS

EPO, European Extended Search Report issued in European Patent Application No. 17180157.4, dated Oct. 2, 2017.
EPO, International Search Report and Written Opinion issued in International Application No. PCT/EP2018/067919, dated Sep. 5, 2018.

* cited by examiner

*Primary Examiner* — Jafar F Parsa
*Assistant Examiner* — Blaine G Doletski
(74) *Attorney, Agent, or Firm* — Norris McLaughlin, P.A.

(57) ABSTRACT

A process for the preparation of a solid composition of an amino acid diacetic acid compound wherein the amino acid diacetic acid compound is methyl glycine-N,N-diacetic acid or a salt thereof, or glutamic N,N-diacetic acid or a derivative thereof, as well as the product obtained by such process are disclosed. The process includes feeding a saturated or oversaturated aqueous composition of the amino acid diacetic acid compound in an aqueous solvent to a drum dryer, wherein the aqueous composition is fed to the drum surface with a layer thickness of from about 0.1 to about 10 mm, the drum has a surface temperature of from about 80 to about 180° C., and the drum operates at a tangential speed of from about 0.1 to about 100 m/min. The method further includes removing the mass from the drum before a full revolution of the drum.

15 Claims, 1 Drawing Sheet

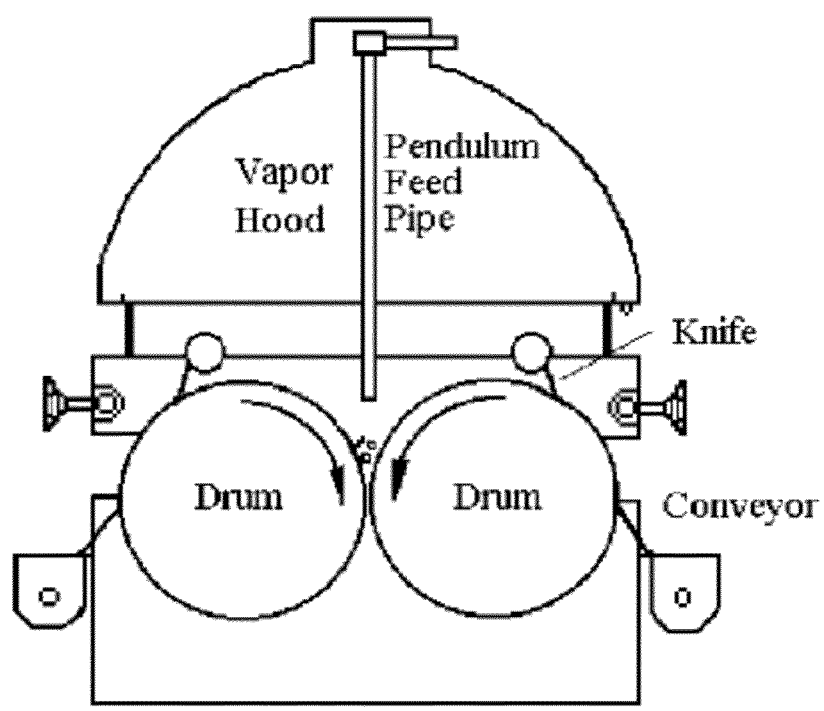
Schematic representation of double drum dryer

PROCESS TO PREPARE A SOLID COMPOSITION OF AN AMINO ACID DIACETIC ACID

CROSS-REFERENCE TO RELATED APPLICATION

This application is a U.S. National-Stage entry under 35 U.S.C. § 371 based on International Application No. PCT/EP2018/067919, filed Jul. 3, 2018, which was published under PCT Article 21(2) and which claims priority to European Application No. 17180157.4, filed Jul. 7, 2017, which are all hereby incorporated in their entirety by reference.

TECHNICAL FIELD

The present invention relates to a process to prepare a solid composition of one or more derivatives of methyl glycine-N,N-diacetic acid or glutamic acid-N,N-diacetic acid and to the compositions obtained therewith.

BACKGROUND

Processes to prepare solid compositions of an amino acid-N,N-diacetic acid are known in the art. A number of documents relate to spraying solutions of the amino acid diacetic acid compounds to obtain them in the solid form, such as WO 2009/103822, WO 2010/133617.

WO2012/168739 discloses a process of spray drying Na3-MGDA starting from a slurry, next agglomerating the obtained solid and subsequently comminuting the obtained agglomerate. The document says that using this process more of the crystalline dihydrate is obtained over the less desired monohydrate. The dihydrate crystal in this document will be referred to as crystal type I and what is called the monohydrate is referred to as crystal type II.

In WO2012/168739 it is shown that for many applications crystal type I is the preferred variety, as it is less hygroscopic than crystal type II and amorphous solids. Powders or granules containing a high degree of type I keep their free-flowing character better upon storage at high humidity conditions, while products containing only or mainly the crystal type II variety fail at these conditions.

It is also known to dry compositions of amino acid-N,N-diacetic acid compounds by applying a layer of an aqueous composition thereof to a surface, heating the applied layer and next removing the then formed cake from the surface.

WO 2010/133618 discloses a process to prepare a solid composition of a glycine-N,N-diacetic acid or glutamine-N,N-diacetic acid derivative wherein an aqueous solution of any of these compounds is concentrated in an evaporator with rotating internals to give a slurry which then is allowed to ripen in a paste bunker and next dried in a thin film drier. The total residence time in the bunker and drier is said to be at least 15 minutes.

WO 2015/173157 discloses a process in which a saturated or oversaturated aqueous solution of methyl glycine-N,N-diacetic acid or glutamic acid-N,N-diacetic acid, seeded with the (desired type of) crystals, is milled at high shear and next applied to a polypropylene substrate, dried under heating at 80° C. and broken from the polypropylene sheet The viscosity of concentrated slurries of amino acid-N,N-diacetic acids is strongly dependent on composition and process conditions. Especially at high concentrations, these slurries show thixotropic behavior, yielding a high risk of blockage of the process stream in the event of fluctuating process conditions. Hence, there remains a desire for processes to prepare solid compositions of amino acid-N,N-diacetic acids that are based on robust equipment and hence have a reduced sensitivity to small differences in composition of the feedstock or processing conditions such as temperature, pressure, residence time and shear and are still able to produce a continuous amount of solid composition with a good flexibility in feedstock and process conditions.

BRIEF SUMMARY

A process for the preparation of a solid composition of an amino acid diacetic acid compound wherein the amino acid diacetic acid compound is methyl glycine-N,N-diacetic acid or a salt thereof, or glutamic N,N-diacetic acid or a derivative thereof, as well as the product obtained by such process are disclosed. The process includes feeding a saturated or oversaturated aqueous composition of the amino acid diacetic acid compound in an aqueous solvent to a drum dryer, wherein the aqueous composition is fed to the drum surface with a layer thickness of from about 0.1 to about 10 mm, the drum has a surface temperature of from about 80 to about 180° C., and the drum operates at a tangential speed of from about 0.1 to about 100 m/min. The method further includes removing the mass from the drum before a full revolution of the drum.

DESCRIPTION OF THE DRAWINGS

FIG. 1 is a schematic representation of double drum dryer, in accordance with an embodiment herein.

DETAILED DESCRIPTION

The present invention now provides a process for the preparation of a solid composition of an amino acid diacetic acid compound wherein the amino acid diacetic acid compound is methyl glycine-N,N-diacetic acid or a derivative thereof, or glutamic acid-N,N-diacetic acid or a derivative thereof, containing a step of feeding an saturated or oversaturated aqueous composition containing the amino acid diacetic acid compound to a drum dryer, wherein the aqueous composition is fed to the drum surface with a layer thickness of 0.1-10 mm, the drum has a surface temperature of 80-180° C., the drum operates at a tangential speed of 0.1-100 m/min and the mass is removed from the drum before a full revolution of the drum.

The present invention also relates to the solid amino acid-N,N-diacetic acid product obtainable by the above process.

In the present process it is possible to employ solutions of the amino acid diacetic acid compound of a broad concentration range. Saturated and oversaturated aqueous compositions in embodiments have concentrations that can lie in the broad range of between 45 and 65 wt %, preferably 55 to 61 wt %, of amino acid-N,N-diacetic acid on total composition.

Drum dryer equipment is simple and thus robust equipment which is not very sensitive to damage, non-uniform feedstocks, or other incidents by which other equipment such as thin film driers would be hampered in continuous operation.

The drum drying process sets itself apart from for example (agitated) thin film evaporation or other contact dryers by the relatively low rotational velocities required, while still featuring efficient heat transfer rates. These mild mechanical conditions result in a robust, reliable and low-maintenance process installation.

Using the process of the invention it is possible to isolate the amino acid-N,N-diacetic acid in the form of a solid showing a high level of crystallinity, while using the drum dryer-based process of the present invention it is also easy to purposively adjust the level of crystallinity in the product formed, by adjusting the process parameters. If the solid composition obtained has a level of crystallinity of 30-50%, an easier compaction is possible than with the 50-75% crystallinity that is normally obtained when using spray granulation techniques. Also, the speed of dissolution increases when a lower crystalline solid composition is prepared in the process of the present invention.

Hence the process of the invention enables easy tailoring of the properties of the product for applications in which MGDA solid plays a role such as automatic dish washer tablets, monoblocks, premixes for feed, and other solid compositions containing the chelating agent based on glutamic acid.

Derivatives of glutamic acid-N,N-diacetic acid and methylglycine-N,N-diacetic acid in accordance with this specification cover both these compounds in their acidic and their salt forms. These salts may have sodium, potassium, ammonium, or a combination of sodium, potassium ammonium and proton as a counterion. In a preferred embodiment the amino acid-N,N-diacetic acid compound is a sodium salt of methylglycine-N,N-diacetic acid, more preferred a disodium salt of MGDA and most preferred the trisodium salt of MGDA.

In another preferred embodiment of the process the aqueous amino acid diacetic acid composition contains 55-61 wt % on total aqueous composition of the amino acid diacetic acid compound. In yet another preferred embodiment the aqueous composition is a slurry, which means that it is an aqueous solution containing solid particles. Slurries form if the concentration of the aqueous amino acid diacetic acid composition exceeds its solubility at a given temperature. In the case of the trisodium salt of MGDA these saturation limits range from ~42% at 20° C. to ~50% at 115° C.

More preferably, the slurry contains solid crystalline particles. Even more preferably, the slurry contains particles of methyl glycine-N,N-diacetic acid of a crystal modification, referred to as crystal type I, that is characterized by the d-values in Angstroms correlating to the respective diffraction angles 2 theta in ° in a X-ray powder diffraction pattern as measured using Cu Kα irradiation as specified in Table 1.

TABLE 1

Crystal Type I and II diffraction patterns

| type I | | type II | |
| --- | --- | --- | --- |
| 2Θ | d (Å) | 2Θ | d (Å) |
| 8.2 | 10.8 | 8.4 | 10.5 |
| 10.5 | 8.4 | 9.5 | 9.3 |
| 15.6 | 5.7 | 11.1 | 8 |
| 16.5 | 5.4 | 13.2 | 6.7 |
| 17.1 | 5.2 | 13.9 | 6.4 |
| 18.1 | 4.9 | 15.8 | 5.6 |
| 18.8 | 4.7 | 16.5 | 5.35 |
| 21 | 4.25 | 16.8 | 5.25 |
| 21.4 | 4.15 | 17.3 | 5.1 |
| 22.6 | 3.9 | 17.7 | 5 |
| 23.7 | 3.75 | 18.9 | 4.7 |
| 24.7 | 3.6 | 20.3 | 4.35 |

In the process of the invention it its preferred that the amino acid diacetic acid is at least 50% in the L-enantiomer form, more preferably it is more than 50% in the L-enantiomer form, most preferably the ratio L-enantiomer: D-enantiomer of the amino acid diacetic acid is between 54:46 and 99:1. This is particularly the case when the amino acid diacetic acid is MGDA in its sodium salt form.

Preferably the drum dryer operates at a tangential speed in the range of 1-25 m/min.

In another preferred embodiment the solid composition is removed from the drum when the drum has completed between 40-90%, even more preferred 40-75% of a full revolution.

Removal is preferably performed using a scraping knife of which the pressure on the drums can be adjusted and controlled. The scraping knife is preferably provided with a system to prevent fouling, like a so-called air-knife, in which case compressed air is directed to the blade of the scraping knife The drum dryer can be a drum dryer of any design, preferably, however, it is a double drum dryer. The drums are preferably plated with chrome in order to prevent product adhesion.

The end plates enclosing the valley between the drums are preferably actively cooled, using e.g. a water-cooling system.

The drum has a preferred surface temperature of 100-160, more preferably 120-150° C.

During the process of the invention the aqueous composition has a residence time in the drum dryer that is preferably less than 10 minutes, wherein the residence time in the drum dryer is the total time between being fed to the equipment, like being introduced to a feeding unit, and being removed from the drum by a scraping unit.

The aqueous composition can be applied to the drum surface by any method used in drum drying, but is preferably performed via nip-feeding. Nip-feeding is a well-defined term for the man skilled in the art, as can be read in Handbook of Industrial Drying—4th Ed., Arnu S Mujamdar (2015) and "Drum drying" Tang Juming et al., in Encyclopedia of Agricultural, Food, and Biological Engineering (2003)

One can feed the nip in the middle of the valley between the drums.

More preferred, however, is using a dosing system that distributes the mass evenly over the drum.

The aqueous composition is typically applied to the nip with a temperature that is close to boiling conditions.

The residence time in the nip can be controlled by variation of feed composition, gap setting, feed temperature, drum temperature, nip size/height and drum speed. Typically, nip residence times may vary between 10-600 seconds, preferably between 200-500, more preferably 100-400 seconds.

Throughout this document diffractograms were recorded using a Bruker-AXS D8 reflection-diffractometer with Ni filtered Cu-Kα radiation. Generator settings are 40 kV, 40 mA. Divergence and anti-scatter slit V20 (variable 20 mm), detector slit 0.6 mm Measuring range: 2Θ=2.0-70.0°, step size 0.02°, time per step 2.2 seconds.

The degree of crystallinity was ascertained from the X-ray powder diffractograms by determining the surface fraction of the crystalline phase and of the amorphous phase and using these to calculate the degree of crystallinity, CD, as the ratio of the area of the crystalline phase, Ic, to the total area, consisting of the area of the amorphous phase, Ia, and the area of the crystalline phase, crystallinity (%): Ic/(Ic+Ia)*100.

This procedure was performed using Bruker EVA v.4.0 software with the following parameters: enhancement disabled, curvature 2.5, threshold 1.

The invention is illustrated by the examples below

Examples 1-6: Drying a Racemic Mixture of a Na3MGDA-Slurry

A racemized solution of methylglycine-N,N-diacetic acid trisodium salt was prepared by heating an aqueous solution of L-MGDA-Na3 40 wt % being 98% enantiomeric pure and containing about 1 wt % NaOH to 230° C. for 15 minutes in order to get full racemization.

between 3.6 barg (~149° C.) and 6.1 barg (~166° C.) and in Table 2 below the pressure is given for each experiment. The residence time on the drum was determined by the rotational speed (R). The minimal and maximal tangential speed of the drum dryer was 3.1-9.4 m/min and in Table 2 below this speed is given for each of the experiments. The dried product was removed from the drum using the scrapers and was collected in two steel troughs. The specific production rate was measured by collecting and weighing the dried product over a distinct period of time. The final assay (A) of the MGDA product was analyzed by titration and XRD analysis was used to verify the crystal structure as well as the crystallinity. Table 2 below indicates the range of process parameters used and the resulting product characteristics.

All samples showed solely the crystalline variety Type I as characterized by the XRD-reflections outlined in Table 1.

TABLE 2

Overview of the key process parameters employed and the characteristics of the products obtained.

| Example | Feed MGDA concentration, F [wt %] | MGDA feed temperature [° C.] | Steam pressure drum, P [barg] | Drum temperature (° C.) | Drum tangential speed (m/min) | Specific production rate, Y [kg/m² · h] | MGDA assay solid product, A [wt %] | Product crystallinity, X [%] |
|---|---|---|---|---|---|---|---|---|
| 1 | 56.2 | 78 | 4.1 | 153 | 3.1 | 26 | 79 | 52 |
| 2 | 60 | 109 | 6.1 | 166 | 6.3 | 31 | 84 | 43 |
| 3 | 58.8 | 111 | 5.8 | 164 | 9.4 | 42 | 81 | 40 |
| 4 | 60 | 112 | 3.6 | 149 | 3.1 | 33 | 79 | 62 |
| 5 | 60 | 112 | 3.6 | 149 | 6.3 | 43 | 77 | 64 |
| 6 | 58.8 | 112 | 4.2 | 153 | 3.1 | 35 | 79 | 55 |

The aqueous racemized solution as so obtained was concentrated until a slurry was obtained containing 56-60 wt % of a racemic mixture of methylglycine-N,N-diacetic acid trisodium salt, to which seeds of the preferred crystal variety type I were added, characterized by the XRD-reflections outlined in the above Table 1. This slurry was used as a feedstock for the drum drying process.

The drum dryer equipment consisted of a double drum dryer (drum diameter 50 cm, length 50 cm) as schematically represented in FIG. 1. The equipment was equipped with chrome plated drums in order to prevent product adhesion. The two drums were hollow cylinders heated by steam in which the temperature could be controlled via the steam pressure. The liquid feed inlet pipe was positioned above the center and between the two drums in the so-called nip. Both ends of the nip were closed with water-cooled plates for prevention of encrustation. Each drum was equipped with one scraper in combination with an air blow system to promote product release from the knife. These scraping units were located at ⅔ of a full revolution of the drum. The water vapor coming from the process was directed towards a ventilation system.

The Na3-MGDA aqueous slurry was fed into the nip. As the slurry came into contact with the steam heated drums there, water started to evaporate further. The slurry level in the nip was controlled manually by adjusting the feed flow from the crystallizer to the drum dryer such that the nip was always filled. The gap size between both drums (referred to as gap setting) was set via a spring, which determined the thickness of the product layer on the drum. The gap setting for this process was ~0.2 mm Once the slurry had passed through the gap, it was dried to its final product assay (A) on the drum surface. The steam pressure (P) was varied By comparing Examples 4 and 5 it is shown that a lower drum speed within the range of the invention results in a somewhat drier product with less remaining water.

By comparing Examples 2 and 5 it is shown that having a drum surface temperature of 149 instead of 166 deg C. results in improved product crystallinity.

Samples obtained from experiments 1, 4 and 6 were stored in a climate chamber at 40° C. and 70% relative humidity, during 24 hours. Upon inspecting the resulting materials it turned out that the samples were all still free-flowing.

Examples 7-8: Drying a L-Enriched Na3MGDA-Slurry

The same drum drying process as described in the previous examples was performed, but now as a feedstock a L-enriched slurry of Na3MGDA was used. This slurry was prepared by heating L-MGDA-Na3 40 wt % being 98% ennatiomeric pure and containing about 1 wt % NaOH to 210° C. for 15 minutes to get a slightly L-enriched sample of which the optical purity was measured by chiral HPLC.

The aqueous racemized solution as so obtained was concentrated until a slurry was obtained containing 56-60 wt % of a racemic mixture of methylglycine-N,N-diacetic acid trisodium salt The enantiomeric ratio of this feedstock was D:L=46/54

In Table 3 the key process parameters employed and the characteristics of the products obtained are presented.

All samples produced showed solely the desired crystalline variety type I as characterized by the XRD-reflections outlined in Table 1.

When processing the racemic mixture (ratio D:L 50:50) relatively inhomogeneous films were deposited, locally varying in thickness. When drying the L-enriched MGDA slurry (ratio D:L 46:54), however, a clearly more homogeneous thin film was cast on the drum, effectively enabling a higher production rate, which is exemplified by comparing Examples 4 and 6, using the racemic mixture, with Examples 7 and 8.

Both sets of experiments were running at similar drum temperatures, and despite the fact that the feed had a lower concentration and a lower temperature, still a higher production rate could be established, while attaining the same product specifications.

Another clear difference observed was that the product obtained was more homogeneous, containing less lumps.

TABLE 3

Overview of the key process parameters employed and the characteristics of the products obtained.

| Example | Feed MGDA concentration, F [wt %] | MGDA feed temperature [° C.] | Steam pressure drum, P [barg] | Drum temperature (° C.) | Drum tangential speed (m/min) | Specific production rate, Y [kg/m² · h] | MGDA assay solid product, A [wt %] | Product crystallinity, X [%] |
|---|---|---|---|---|---|---|---|---|
| 7 | 57.3 | 109 | 3.6 | 149 | 7.9 | 49 | 79 | 60 |
| 8 | 57.3 | 107 | 4.1 | 153 | 11.0 | 63 | 78 | 58 |

Comparative Examples 9-12 Preparation of Solid Na3-MGDA in a Thin Film Dryer

A slurry containing 54-60 wt % of racemic methyl glycine-N,N-diacetic acid trisodium salt, solely containing seeds of the preferred crystal variety type I, characterized by the XRD-reflections outlined in Table 1, was fed to a horizontal thin film dryer.

For a schematic overview of the thin film dryer equipment used, reference is made to Kirk-Othmer Encyclopedia of Chemical Technology, chapter "Drying" by Arun Mujumdar, FIG. 23 on page 40.

The thin film dryer had a heat exchanging surface of approx. 0.5 m2. Agitation took place with a tip speed of 8 m/s and an agitator-wall spacing of approx. 2 mm. This equipment is very similar in set-up to the Buss horizontal thin film drier referred to in patent WO 2010/133618. The unit was run under vacuum with an outgoing vapor temperature of 50° C. The steam fed to the dryer's jacketed wall had a temperature of 165° C. The table below indicates the range of process parameters used and the resulting product characteristics. The final assay (A) of the MGDA product was analyzed by titration and XRD analysis was used to verify the crystal structure as well as the crystallinity. Table 4 below indicates the range of process parameters used and the resulting product characteristics. All samples produced showed the presence of two crystalline varieties as characterized by the XRD-reflections outlined in Table 4.

TABLE 4

Overview of the crystallization-thin film dryer tests defined by key process parameters and final product characteristics.

| Example | Feed MGDA concentration, F [wt %] | Feed MGDA temperature, $T_{feed}$ [° C.] | Steam temperature, T [° C.] | MGDA assay solid product, A [wt %] | Product crystallinity, X [%] | Crystal form II [%] |
|---|---|---|---|---|---|---|
| 9 | 54 | 90 | 165 | 83 | 52 | 6 |
| 10 | 54 | 76 | 165 | 84 | 67 | 6 |
| 11 | 56 | 76 | 165 | 85 | 66 | 12 |
| 12 | 61 | 88 | 165 | 83 | 66 | 12 |

Humidity Test

The samples obtained from thin film dryer examples 9 to 12, showing an overall crystallinity in de range of 65-70%, but containing 8-12% of the crystal type II variety, were stored in a climate chamber at 40° C. and 70% relative humidity, during 24 hours. Upon inspecting the resulting materials it turned out that the samples obtained from the thin film dryer were caked strongly.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A process for the preparation of a solid composition of an amino acid diacetic acid compound wherein the amino acid diacetic acid compound is methyl glycine-N,N-diacetic acid or a salt thereof, or glutamic N,N-diacetic acid or a derivative thereof, containing a step of
    feeding a saturated or oversaturated aqueous composition of the amino acid diacetic acid compound in an aqueous solvent to a drum dryer, wherein the aqueous composition is fed to the drum surface with a layer thickness of 0.1-10 mm, the drum has a surface temperature of 80-180° C., and the drum operates at a tangential speed of 0.1-100 m/min; and
    the mass is removed from the drum before a full revolution of the drum.

2. The process of claim 1 wherein the aqueous composition contains from about 45 to about 65 wt % of the amino acid diacetic acid compound on total aqueous composition.

3. The process of claim 1 wherein the amino acid diacetic acid compound is a sodium salt of methylglycine-N,N-diacetic acid.

4. The process of claim 1 wherein the composition contains from about 55 to about 65 wt % of the amino acid diacetic acid compound on total aqueous composition.

5. The process of claim 1 wherein the drum operates at a tangential speed of from about 1 to about 25 m/min.

6. The process of claim 1 wherein the solid composition is removed from the drum when the drum has completed between from about 40 to about 75% of a full revolution.

7. The process of claim 1 wherein the drum dryer is a double drum dryer.

8. The process of claim 1 wherein the drum has a surface temperature of 100-160° C.

9. The process of claim 1 wherein the aqueous composition has a residence time in the drum dryer of less than about 10 minutes.

10. The process of claim 1 wherein the aqueous composition is applied to the drum surface using nip-feeding.

11. The process of claim 1 wherein the aqueous composition is a slurry.

12. The process of claim 11 wherein the aqueous composition is a slurry containing crystals of the amino acid diacetic acid compound.

13. The process of claim 12 wherein the amino acid diacetic acid compound is the trisodium salt of MGDA and the crystals have the below crystal modification characterized by the d-values in angstroms corresponding to the respective diffraction angles 2 theta in ° in a X-ray powder diffraction pattern measured using Cu Kα irradiation shown below:

| 2Θ | d (Å) |
|---|---|
| 8.2 | 10.8 |
| 10.5 | 8.4 |
| 15.6 | 5.7 |
| 16.5 | 5.4 |
| 17.1 | 5.2 |
| 18.1 | 4.9 |
| 18.8 | 4.7 |
| 21 | 4.25 |
| 21.4 | 4.15 |
| 22.6 | 3.9 |
| 23.7 | 3.75 |
| 24.7 | 3.6 |

14. The process of claim 1 wherein the amino acid diacetic acid is at least about 50% in the L-enantiomer form.

15. The process of claim 14 wherein the ratio L-enantiomer:
D-enantiomer of the amino acid diacetic acid is between from about 54:46 and to about 99:1.

* * * * *